United States Patent
Matsuura (10) Patent No.: US 8,353,887 B2
(45) Date of Patent: Jan. 15, 2013

(54) SPERM COLLECTION DEVICE

(75) Inventor: Tsutomu Matsuura, Nakano-ku (JP)

(73) Assignee: Tenga Co., Ltd., Nakano-ku (JP)

( * ) Notice: Subject to any disclaimer, the term of this patent is extended or adjusted under 35 U.S.C. 154(b) by 432 days.

(21) Appl. No.: 12/663,054

(22) PCT Filed: Jun. 4, 2008

(86) PCT No.: PCT/JP2008/060264
§ 371 (c)(1),
(2), (4) Date: Dec. 4, 2009

(87) PCT Pub. No.: WO2008/149883
PCT Pub. Date: Dec. 11, 2008

(65) Prior Publication Data
US 2010/0174257 A1    Jul. 8, 2010

(30) Foreign Application Priority Data
Jun. 6, 2007    (JP) .................................. 2007-150925

(51) Int. Cl.
*A61F 5/44*    (2006.01)
(52) U.S. Cl. .......... 604/347; 604/349; 600/38; 128/880; 128/844; 602/22; 602/63
(58) Field of Classification Search ................... 604/347, 604/349; 600/38; 128/880, 844; 602/22, 602/63
See application file for complete search history.

(56) References Cited

U.S. PATENT DOCUMENTS

| | | | | |
|---|---|---|---|---|
| 1,383,944 A | * | 7/1921 | Hart | 600/39 |
| 3,456,965 A | * | 7/1969 | Harrison et al. | 285/260 |
| 3,547,102 A | | 12/1970 | Frenkel | |
| 3,866,611 A | * | 2/1975 | Baumrucker | 128/885 |
| 5,184,629 A | * | 2/1993 | Erickson et al. | 128/885 |
| 5,437,652 A | * | 8/1995 | Anatolievich | 604/349 |
| 5,571,125 A | * | 11/1996 | Chadwick | 606/157 |
| 5,782,818 A | * | 7/1998 | Shubin | 604/349 |
| 5,860,911 A | * | 1/1999 | Dolade Guardia | 600/39 |
| 5,885,233 A | * | 3/1999 | Adachi | 601/138 |
| 6,113,532 A | * | 9/2000 | Yap | 600/38 |
| 6,149,580 A | * | 11/2000 | Dabney | 600/38 |
| 6,719,714 B2 | * | 4/2004 | Sossong | 602/30 |
| 7,041,064 B2 | * | 5/2006 | Vayer | 600/562 |
| 7,658,195 B2 | * | 2/2010 | Dennis | 128/885 |

(Continued)

FOREIGN PATENT DOCUMENTS

JP    3053484 U    10/1998

(Continued)

OTHER PUBLICATIONS

Patent Abstracts of Japan, Publication No. 2006-334176, dated Dec. 14, 2006, 1 page.

(Continued)

*Primary Examiner* — Tatyana Zalukaeva
*Assistant Examiner* — Ginger T Chapman
(74) *Attorney, Agent, or Firm* — Masuvalley & Partners (57) ABSTRACT

A sperm collection device includes an open/close unit including two open/close members openably and closably supported about a hinge and core pieces supported by the open/close members. The core pieces are configured to open and close with the open/close members and to form an insertion space when the open/close members are closed.

20 Claims, 7 Drawing Sheets

U.S. PATENT DOCUMENTS

| | | | | |
|---|---|---|---|---|
| 7,753,895 | B2* | 7/2010 | Matsuura | 604/349 |
| 7,993,315 | B2* | 8/2011 | Matsuura | 604/349 |
| 2007/0031895 | A1 | 2/2007 | Herr et al. | |
| 2007/0073205 | A1* | 3/2007 | Hull et al. | 602/22 |
| 2008/0004654 | A1* | 1/2008 | Tomlinson | 606/201 |
| 2010/0069706 | A1* | 3/2010 | Rousere | 600/33 |
| 2010/0222793 | A1* | 9/2010 | Skipper | 606/151 |

FOREIGN PATENT DOCUMENTS

| | | | |
|---|---|---|---|
| JP | 3076627 | U | 4/2001 |
| JP | 2006-334176 | A | 12/2006 |
| JP | 2006-340870 | A | 12/2006 |
| JP | 2006-340871 | A | 12/2006 |
| WO | 2006/129728 | A1 | 12/2006 |
| WO | 2006/132125 | A1 | 12/2006 |

OTHER PUBLICATIONS

Patent Abstracts of Japan, Publication No. 2006-340870, dated Dec. 21, 2006, 1 page.

Patent Abstracts of Japan, Publication No. 2006-340871, dated Dec. 21, 2006, 1 page.

International Search Report issued in PCT/JP2008/060264, mailed on Jul. 1, 2008, with translation, 2 pages.

Supplementary European Search Report and European Search, Issued on Nov. 9, 2011, EP Patent Application No. 08765077.6, European Patent Office.

* cited by examiner

SPERM COLLECTION DEVICE

TECHNICAL FIELD

The present invention relates to a sperm collection device, and more particularly to an improvement of a sperm collection device which has been conventionally used based on requirements for a medical research and a treatment and on a social requirement for prevention of a sex crime, prostitution, and spreading of sexually-transmitted disease, and the like.

BACKGROUND ART

There are proposed various sperm collection devices for obtaining men's sperm from a necessity of a medical research and a treatment. The sperm collection devices are used for a medical necessity, for example, examining a husband's sexual function from sperm collected to investigate a cause of conjugal infertility, treating sexual dysfunction, and securing sperm for artificial insemination. There is conventionally known a simple sperm collection device which can be obtained at a low cost and does not cause a hygienic and health problems because it is a disposable type to satisfy various social needs such as prevention of a sexual crime, a prostitution, a decrease in the number of sexually-transmitted disease infected patients, and the like by solving a personal sexual desire.

Further, recently, an attention is paid to sexual desire processing of not only healthy persons but also elderly persons and impaired persons in nursing and personal care facilities and the like, and thus a development of a simple sperm collection device which can satisfy the requirements is demanded.

Japanese Utility Model Registration No. 3076627 (Patent Document 1), for example, discloses a sperm collection device arranged such that an interior member (core member) composed of gel-like synthetic resin (styrene thermoplastic elastomer) and having a deep concave space therein is disposed in a cylindrical vessel main body, small projections and bag-like portions, which project into the concave space, are disposed to an inner surface of the interior member and an exterior member composed of urethane resin is disposed to cover a periphery of the interior member. In the sperm collection device, after an assembly, to which the exterior member is assembled to cover the periphery of the interior member, is inserted into the vessel from an opening formed to one end of the cylindrical vessel main body, the opening of the vessel is sealed with a cap. When the sperm collection device is used, sperm is collected by gripping the vessel main body in a state that a penis is inserted into a concave space of the interior member stored in the vessel main body by removing the cap and performing a reciprocating operation for rubbing the penis.

However, since this type of the sperm collection device has such a structure that the bag-like interior member is fixed in the vessel main body, it is difficult to take out only the interior member. Accordingly, the sperm collection device is not suitable to repeatedly use the interior member without a hygienic problem by rinsing the inside thereof and thus basically a disposable type. As a result, the sperm collection device is disadvantageous in a cost performance and a load on an environment. Even if the concave space in the interior member stored in the vessel main body is forcibly rinsed, since it is difficult to entirely rinse it, a repeated use thereof is unhygienic. Since the interior member is completely stored in the hard vessel main body, an outer surface of the interior member cannot be touched with a hand while the penis is being rubbed. Thus, it is difficult to adjust a degree of pressure applied to the penis and a portion to which pressure is applied by band. Further, when the interior member having the bag-like arrangement is manufactured by injection molding, it is difficult to form a complex shape (a projection, a fold, and the like) to the inside of the interior member when it is taken into consideration to remove the interior member from a mold, and the like.

In contrast, since it is impossible to sufficiently apply tightening force to the penis unless the interior member is stored in the vessel main body composed of hard resin, the arrangement for storing the interior member in the vessel main body is indispensable.

Patent Documents 2 to 4 sperm collection devices are arranged such that a core member composed of gel-like resin is stored in a vessel main body as well as the core member is positioned in the vessel main body by bonding and fixing an outside periphery of a sponge lid attached to an extreme end surface of the core member to an inner wall of the vessel main body.

However, even these sperm collection devices have the same problem as that of Patent Document 1.

Patent Document 1: Japanese Utility Model Registration No. 3076627
Patent Document 2: Japanese Patent Application Laid-Open No. 2006-334176
Patent Document 3: Japanese Patent Application Laid-Open No. 2006-340870
Patent Document 4: Japanese Patent Application Laid-Open No. 2006-340871

DISCLOSURE OF THE INVENTION

As described above, the conventional sperm collection device is disadvantageous in the cost performance and the load on the environment because it is basically the disposable type and cannot be repeatedly used due to its arrangement for fixedly storing the core member composed of soft resin in the vessel composed of the hard resin. Further, since a user cannot touch an outer surface of the core member while he uses the sperm collection device, a problem arises also in a feeling of use in that a stimulus to a penis cannot be controlled.

One or more embodiments of the present invention provide a sperm collection device which can be repeatedly used without a hygienic problem because a core member can be easily rinsed while maintaining a merit of storing the core member in a vessel and can arbitrarily control a stimulus applied to the core member by hand while a rubbing operation is performed.

SUMMARY OF THE INVENTION

The invention according to a first aspect is characterized by having an open/close unit composed of two open/close members openably and closably supported about one end and core pieces opened and closed by being supported by the open/close members, respectively for forming an insertion empty space between the closed core pieces.

Since the two core pieces constitute a bag-like core member when they are closed and insertion empty space is opened when the core pieces are opened, the core pieces can be easily rinsed. Further, since the core pieces can be easily manufactured by injection molding, an arbitrary layout can be employed as a shape of an inner surface of the insertion empty space.

Further, an invention according to a second aspect further includes a holder for detachably supporting the open/close unit in a closed state.

An invention according to a third aspect is characterized in that when the open/close members are closed, they form a cylindrical hollow portion therein in the first aspect.

Since the open/close members form the cylindrical hollow portion when they are closed, a shape of them is kept by storing the core pieces (core member) composed of a soft material in the cylindrical hollow portion to keep a good shape so that deformation, a deformed shape, and horizontal deformation can be prevented.

An invention according to a fourth aspect is characterized in that when the core pieces are closed, they are made to a cylindrical member and stored in a cylindrical hollow portion of the open/close members in the second aspect.

An invention according to a fifth aspect is characterized in that inner side surfaces of the core pieces which form the insertion empty space at least when they are closed are composed of gel-like resin or other soft resin material in the first, second, or third aspect.

An invention according to a sixth aspect is characterized in that the core pieces have such an arrangement that outer surfaces of built-in members composed of a hard elastic material are covered with a soft resin material in any one of the first to fourth aspects.

An invention according to a seventh aspect is characterized in that a hollow space is formed between at least a part of the outer surface of the built-in member and the soft resin material in the fifth aspect.

An invention according to an eighth aspect is characterized in that openings are formed on outer peripheral surfaces of the open/close members and parts of the core pieces are exposed in the openings in any one of the first to sixth aspects.

An invention according to a ninth aspect is characterized in that the holder, which has a base portion disposed to one end in an axial direction and includes a flat bottom surface, and at least two hold portions which extend from the base portion in the axial direction and guide mounting/dismounting of the open/close unit in the closed state as well as hold the open/close unit in a state of storage and in a state of use, respectively so that it cannot be removed in any one of the first to seventh aspects.

According to one or more embodiments of the present invention, since the two core pieces for constituting the bag-like core member are arranged by assembling them in place of arranging the core member from a bag member, the core pieces can be completely rinsed in a state that insides of the core pieces are exposed. As a result, the sperm collection device can be repeatedly used without a hygienic problem. It is difficult to perform rinsing when a bag-like core member composed of soft resin is disposed in a hard vessel as in the conventional sperm collection device. However, according to one or more embodiments of the present invention, the core member can be repeatedly rinsed although the core pieces are stored in the hard vessel, and thus the sperm collection device can be repeatedly used without a hygienic problem.

Further, since a lotion can be also coated in the concave space before the core pieces are closed, it can be entirely injected therein and workability can be enhanced.

Further, since the core member is formed in the non-bag state and the concave space is exposed when the core member is opened, a metal mold having a simple structure can be used when the core pieces are manufactured by injection molding. As a result, a feeling of use can be improved because a variation such as complex projections, folds, and the like can be easily formed as an inner surface shape of the core pieces.

Further, since a feeling of tightening to a penis can be maintained because the core pieces are held by the relatively hard open/close members as well as a feeling of use can be improved by adjusting pressure by pressing the outer surfaces of the exposed core pieces by hand.

Besides for medical purposes, the sperm collection device in accordance with one or more embodiments of the present invention can be used as a means for satisfying important social requirements, such as improving the quality of life (QOL) for elderly men and disabled persons.

EXPLANATION OF REFERENCE NUMERALS

1 . . . sperm collection device, 2 . . . open/close unit, 3 . . . hinge, 4 . . . open/close member, 4a . . . insertion opening, 5 . . . cylindrical hollow portion, 5a . . . concave portion, 6 . . . opening, 7 . . . end edge, 7A . . . projection, 7a . . . projection, 10 . . . core piece, 11 . . . insertion empty space, 11a . . . insertion inlet, 12 . . . inner shell (built-in member), 13 . . . soft resin layer, 5a . . . concave portion, 16 . . . concave portion, 17 . . . hollow space, 30 . . . holder, 31 . . . base portion, 31a . . . bottom surface, 35 . . . hold portion, 36 . . . guide member

DETAILED DESCRIPTION

The present invention will be described below in detail by an embodiment shown in drawings. Numerous specific details are set forth in order to provide a more thorough understanding of the invention. However, it will be apparent to one of ordinary skill in the art that the invention may be practiced without these specific details. In other instances, well-known features have not been described in detail to avoid obscuring the invention.

Figure 1A:
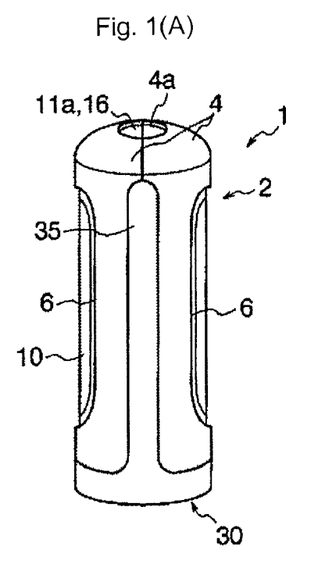
FIGS. 1(a) and (b) are perspective views showing an assembled state of a sperm collection device according to an embodiment of the present invention.
Figure 1B:
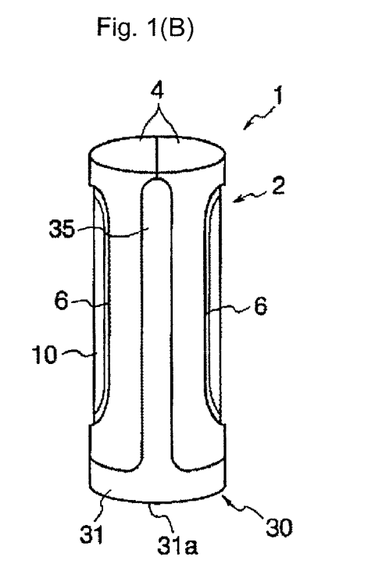
Figure 2:
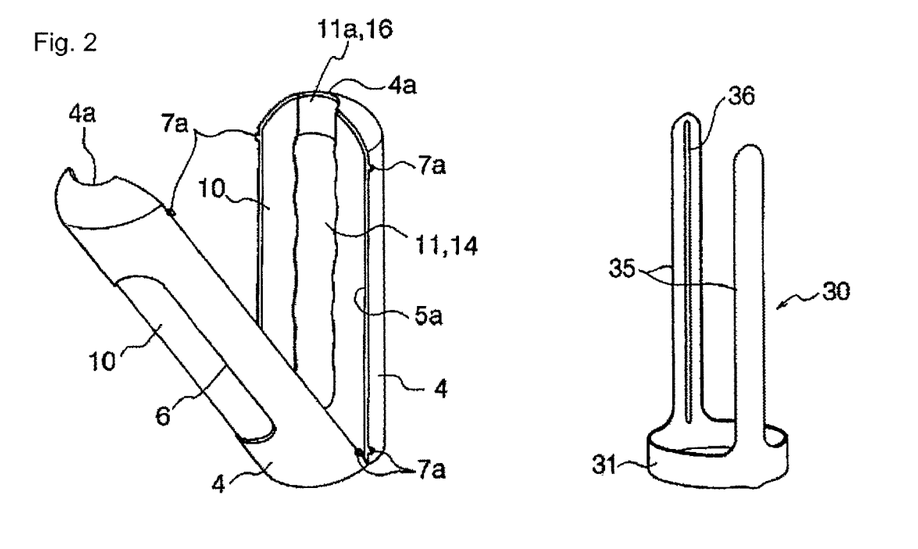
FIG. 2 is a perspective view showing a state that an open/close unit and a holder, which constitute the sperm collection device according to an embodiment of the present invention, are separated from each other.
Figure 3:
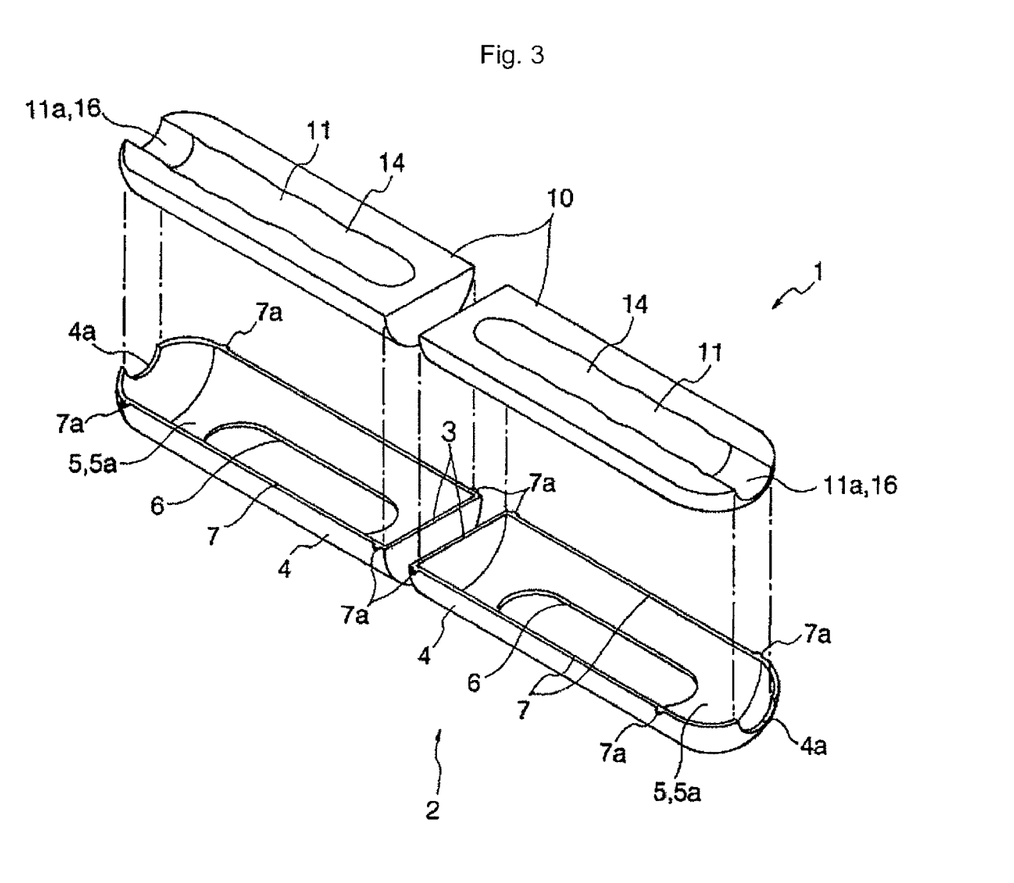
FIG. 3 is an exploded perspective view showing an arrangement of the open/close unit in accordance with an embodiment of the present invention.

FIGS. 1(a) and (b) are perspective views showing an assembled state of a sperm collection device according to an embodiment of the present invention, FIG. 2 is a perspective view showing a state that an open/close unit and a holder, which constitute the sperm collection device, are separated from each other, and FIG. 3 is an exploded perspective view showing an arrangement the open/close unit.

The sperm collection device 1 is composed of the open/close unit 2 and the holder 30. The open/close unit 2 is composed of two open/close members 4 openably and closably supported about a hinge 3 in one end in an axial direction and core pieces 10 supported by the open/close members 4, respectively and opened and closed together with the open/close members, and a penis insertion empty space 11 is formed between the core pieces 10 closed as shown in FIG. 1. The holder 30 detachably holds the open/close unit 2 in a closed state in both states of a state of use (FIG. 1(a)) and a state of storage (FIG. 1(b)), respectively. In the state of use shown in FIG. 1(a), a penis insertion inlet 11a is opened so that it can be used. In the state of storage shown in FIG. 1(b), since the penis insertion inlet 11a is closed by the holder 30 on the contrary, it cannot be used.

The open/close members 4 are composed of a relatively hard resin sheet and concave portions 5a are formed inside of the open/close members 4 so that a cylindrical hollow portion 5 is formed inside thereof when they are closed as shown in FIG. 1. Semi-cylindrical core pieces 10 are engaged with each other and stored in the concave portions 5a in an alignment state. Since the open/close members form the cylindrical hollow portion when they are closed, a shape of them is kept by storing the core pieces (core member) composed of a soft material in the cylindrical hollow portion to keep a good shape so that deformation, a deformed shape, and horizontal deformation can be prevented. Openings 6 are formed to parts of side surfaces of the open/close members 4 so that parts of outer surfaces of the core pieces 10 are exposed therethrough. A shape and an opening area of the openings 6 can be arbitrarily set so that a user can apply pressure to parts of the exposed core pieces with a finger. The openings 6 are not indispensable, and an arrangement for covering overall peripheral surfaces of the core pieces with the open/close members may be employed so that they are not exposed. Note that the two open/close members 4 constitute a vessel.

The hinge portion 3 may be arranged as a coupling piece which is molded integrally with the open/close members 4 when they are molded or may be attached later.

At least parts of the core pieces 10 are composed of soft resin such as gel-like resin and the like, and the open/close members 4 are fixed to the core pieces 10 by an arbitrary method. As shown in a sectional view of FIG. 5, the core pieces 10 of the embodiment have such an arrangement that an overall outer surfaces of inner shells (built-in members) 12, which are composed of curved thin-sheet-like relatively hard resin, is covered with soft resin layers 13, and concave portions 14 are formed around insides of the concave portions 10 to form the insertion empty space 11. Concave portions 16 acting as the insertion inlet 11a are formed to one ends in an axial direction of the concave portions 14. Note that insertion openings 4a are formed to end surfaces of the open/close members 4 corresponding to the insertion inlet 11a. Note that each opening 4a may have such as shape that the insertion inlet 11a is entirely exposed therethrough. Further, the insertion inlet 11a may be closed by soft resin constituting a peripheral edge portion of the insertion inlet at an ordinary time, and the insertion openings 4a may be closed by soft resin forming the insertion inlet 11a.

Further, insertion side end portions of the open/close members 4 may be cut a predetermined length to shorten the lengths thereof so that insertion side end portions (arc-shaped portions having the insertion inlet 11a) of the core pieces are exposed (projected) to the outside of the open/close members at all times.

The soft resin constituting the core pieces 10 is composed of gel-like elastic resin such as elastomer, gel-like rubber, and the like. Since the core pieces 10 are not formed in a bag-like shape different from a conventional core member and have a shape obtained by dividing a bag member into two portions in an axial direction, a metal mold used for injection molding can be simplified. Accordingly, projections, folds, and the like, which are arbitrarily disposed and have arbitrary shapes, are formed on inner walls of the concave portions 14. Note that the two core pieces 10 constitute the core member.

Figure 5A:
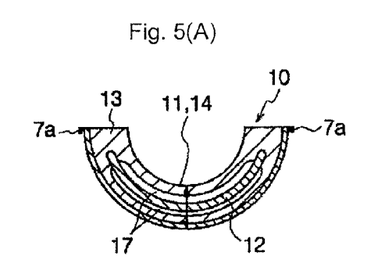
FIGS. 5(a) and (b) are sectional views showing an internal structure of a core piece supported by one open/close member in accordance with an embodiment of the present invention.
Figure 5B:
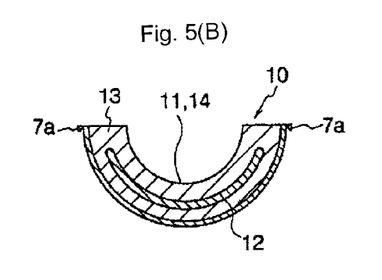
Figure 6A:
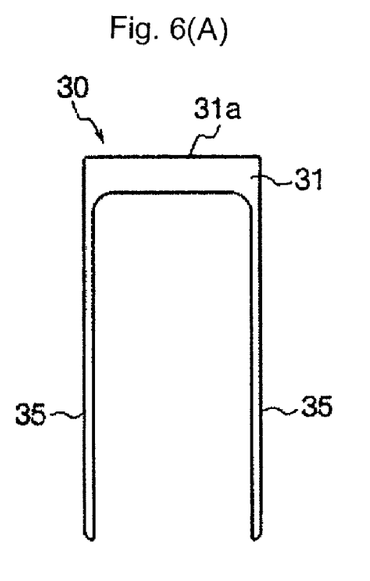
FIGS. 6(a) to (d) are a front elevational view, a plan view, a bottom view, and a side elevational view, respectively, showing an arrangement of a holder constituting the sperm collection device according to an embodiment of the present invention.
Figure 6B:
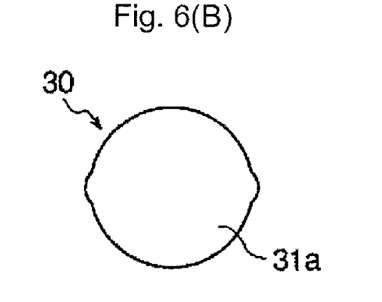
Figure 6C:
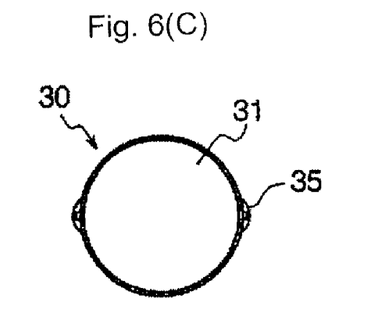
Figure 6D:
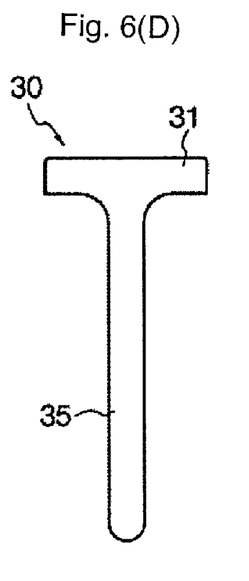
Figure 7A:
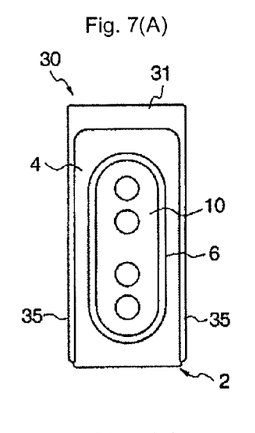
FIGS. 7(a) to (e) are a front elevational view, a plan view, a bottom view, a side elevational view, and a sectional view of the main portion, respectively, showing an arrangement of the sperm collection device according to an embodiment of the present invention.
Figure 7B:
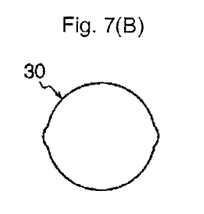
Figure 7C:
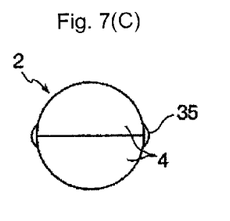
Figure 7D:
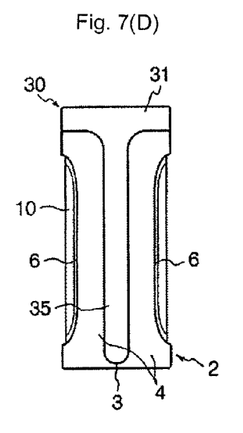
Figure 7E:
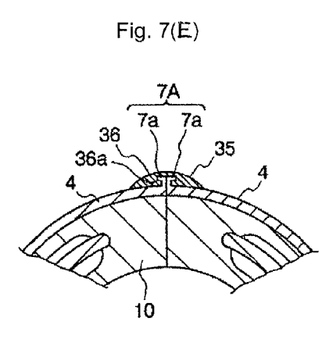

Further, as shown in FIG. 5(a), since the inner shells (built-in members) 12, which are disposed in the core pieces corresponding to the openings 6 of the open/close member 4 and composed of a hard elastic material, have a full-floating structure which is caused to float by being supported by soft resin (FIGS. 5(a) and (b)), and the structure allows the inner shells 12 to be induced in a thickness direction in a wall thickness portions of the core pieces 10. With this arrangement, when the inner shells are pressed in an inside diameter direction, a sperm collection effect can be enhanced by arbitrarily and appropriately applying pressure and a stimulus to a penis which reciprocates in the insertion empty space 11. In this case, when hollow spaces 17 are formed inside (or/and outside) of the inner shells 12 (FIG. 5(a)), since the hollow spaces act as air cushions, the pressure and the stimulus can be applied delicately. Otherwise, it is also possible to employ such a design that the pressure and the stimulus can be directly felt by integrally covering the overall inner shells with the soft resin constituting the core pieces without forming the hollow spaces (FIG. 5(b)).

As shown in FIG. 6, the holder 30 has a base portion 31, which includes a flat bottom surface 31a formed to its one end in an axial direction, and at least two hold portions 35 which extend from the base portion 31 in the axial direction in the axial direction and guide mounting/dismounting of the open/close unit 2 in the closed state as well as hold the open/close unit so that it cannot be removed.

Figures 4A, 4C:
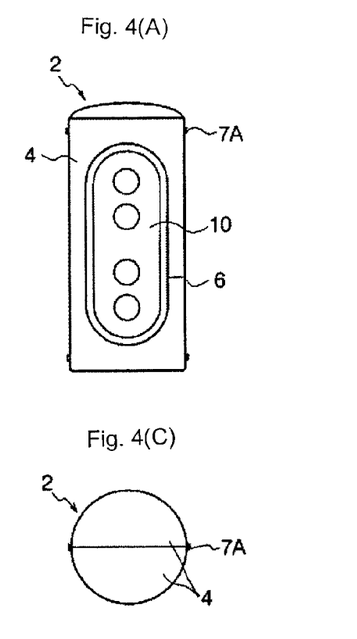
FIGS. 4(a) to (d) are a front elevational view, a plan view, a bottom view, and a side elevational view, respectively, showing an arrangement of the open/close unit constituting the sperm collection device according to an embodiment of the present invention.
Figure 4B:
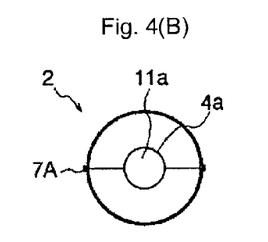
Figure 4D:
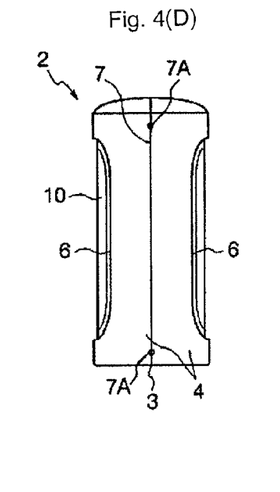

Projections 7a each having an L-shaped cross section are formed to end edges 7 of the open/close members 4 which come into an intimate contact with each other when they are closed, and when the open/close members are closed as shown in FIG. 4, the projections 7A approach to each other and form projections 7A each having a T-shaped cross section. In this case, the projections 7a may be formed to necessary portions of the end edges 7 or may be formed as long projections extending in the entire length of the end edges 7 or to parts thereof.

FIGS. 7(a) to (e) are views explaining a state that the holder is assembled to the open/close unit. As shown in an enlarged sectional view of a main portion of FIG. 7(e), guide members 36 are formed on inner side surfaces of the hold portions 35 of the holder so that they receive and guide the projections 7A. Since the guide members 36 have T-shaped empty spaces 36a capable of receiving the projections 7A each having the T-shaped cross section shape, the guide members can receive the projections 7A from openings of one ends in the axial direction of the T-shaped empty spaces 36a thereof and guide the projections 7A in the axial direction. Since the projections 7A each composed of the two projections 7a are guided while being pressed so that guide members 36 are not separated therefrom, the open/close members 4 can be held by the holder 30 without being separated therefrom.

Figure 8A:
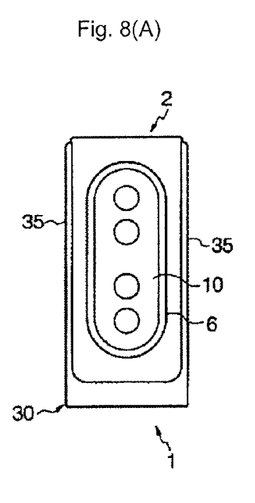
FIGS. 8(a), (b), and (c) are views showing a manipulation procedure in accordance with an embodiment of the present invention.
Figure 8B:
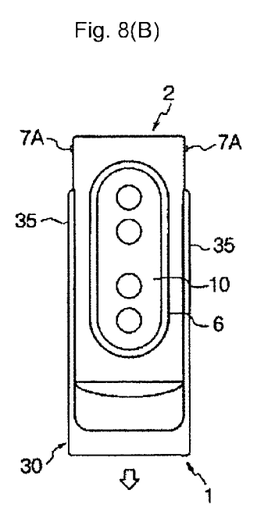
Figure 8C:
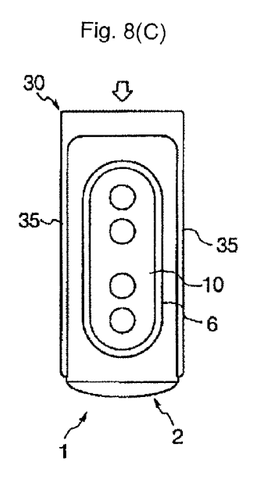

FIG. 8(a) shows a state that the holder 30 holds the open/close unit 2, which is in the closed state, in a state of storage (state of non-use), FIG. 8(b) shows a procedure for removing the holder from the open/close unit, and FIG. 8(c) shows a state that the open/close unit is held in a state of use. In the state of use of FIG. 8(c), the penis can be inserted into the insertion empty space 11 from the insertion opening 4a and the insertion inlet 11a.

Figure 9A:
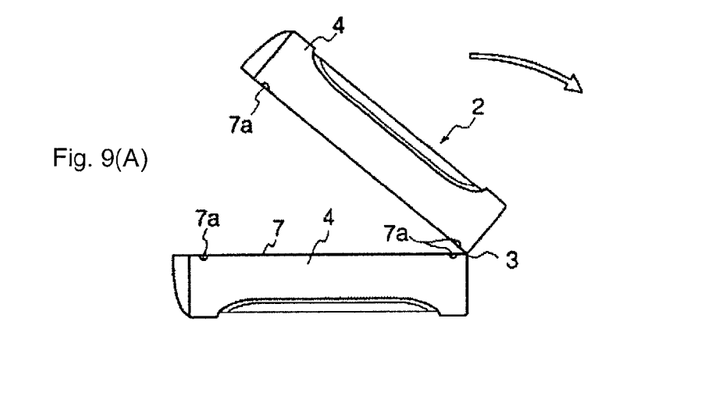
FIGS. 9(a), (b), and (c) are views of an open/close procedure of the open/close unit and a state that the open/close unit is being dried in accordance with an embodiment of the present invention.
Figure 9B:
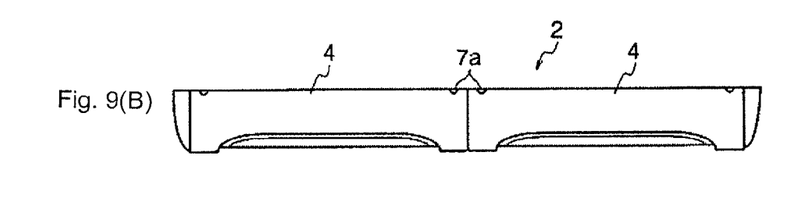
Figure 9C:
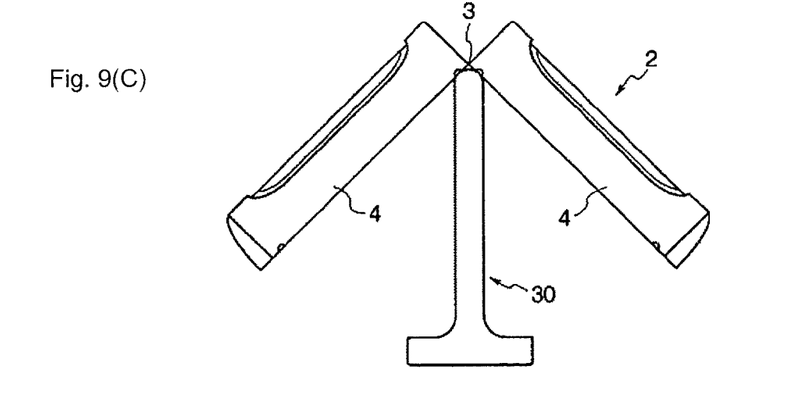

The open/close unit 2 can be opened from the closed state as shown in FIG. 4 and the like by a sequence shown in FIGS. 9(a) and (b). In the open state, since inner side surfaces of the core pieces are exposed, insides of the concave portions 14 can be entirely rinsed. After the concave portions 14 are rinsed, they can be dried by holding an intermediate portion of the open/close unit 2 opened in a V-shape on an upper end portion of the hold portions 35 in a state that the bottom surface of the base portion 31 is placed on a flat surface as shown in FIG. 9(c). Cutouts, projections, and the like are formed on upper end portions of the hold portions 35 so that the intermediate portion of the open/close unit 2 can be easily held.

After the concave portions 14 are dried, the open/close unit 2 is closed, attached to the holder, and can be stored in the state of storage of FIG. 8(a) or can be placed in the state of use of FIG. 8(c). The sperm collection device is used by injecting a lotion from the insertion inlet 11a. Otherwise, the lotion may be coated in the concave portions 14 of the core pieces before the open/close unit 2 is closed.

According to the sperm collection device of the present invention having the above arrangement, since the open/close unit 2 can be opened, the insides of the core pieces can be entirely rinsed in a state that they are opened, the sperm collection device can be repeatedly used without a hygienic problem. Rinsing is difficult when a bag-like core member composed of soft resin is disposed in a hard vessel as in a conventional sperm collection device. In the present invention, however, the sperm collection device can be rinsed although the core pieces are stored in the hard vessel, and can be repeatedly used.

Since the lotion can be coated in the concave portions 14 before the core pieces are closed, it can be entirely injected thereinto. Thus, workability can be enhanced.

Further, the core member is formed in the non-bag shape and is such a type that the concave portions 14 are exposed when the open/close unit 2 is opened. Accordingly, when the core pieces 10 are manufactured by injection molding, since a metal mold having a simple structure can be used, a variation such as formation of a complex projection, folds, and the like can be provided with an inner surface shape of the core pieces so that a feeling of use can be enhanced.

Further, since the core pieces are held by the relatively hard open/close members, a feeling of tightening to a penis can be maintained. In contrast, since outer surfaces of the core pieces are exposed from the openings 6, the feeling of use can be enhanced by adjusting pressure by pressing the outer surfaces of the exposed core pieces with a hand.

The invention claimed is:
1. A sperm collection device comprising:
   an open/close unit comprising:
      two open/close members openably and closably supported about a hinge; and
      core pieces, each open/close member supporting one core piece, the core pieces comprised of a material more flexible than a material constituting the open/close members;
   wherein the core pieces are configured to open and close with the open/close members and to form an insertion space when the open/close members are closed;
   wherein the open/close members form a cylindrical hollow portion internally therein when the open/close members are closed; and
   wherein the core pieces are stored in the cylindrical hollow portion of the open/close members.

2. The sperm collection device according to claim 1, wherein, when the core pieces are closed, the core pieces form a cylinder.

3. The sperm collection device according to claim 1, wherein inner side surfaces of the core pieces that form the insertion space when the core pieces are closed are composed of soft resin material.

4. The sperm collection device according to claim 1, wherein an outer surface of internal portions of the core pieces are composed of hard elastic material and are covered with soft resin material.

5. The sperm collection device according to claim 4, wherein a hollow space is formed between at least a part of the outer surface of the internal portions of the core pieces and the soft resin material.

6. The sperm collection device according to claim 1, wherein
   openings are formed on outer peripheral surfaces of the open/close members, and
   at least a portion of the core pieces is exposed in the openings.

7. The sperm collection device according to claim 1, further comprising a holder for detachably supporting the open/close unit in a closed state;
   wherein the holder comprises:
      a base portion disposed at one end in an axial direction and includes a flat bottom surface; and
      at least two hold portions that extend from the base portion in an axial direction,
   wherein the at least two hold portions are configured to guide a mounting/dismounting of the open/close unit in the closed state and to hold the open/close unit in place in a state of storage or in a state of use so that the open/close unit cannot be dismounted.

8. The sperm collection device according to claim 1, further comprising a holder for detachably supporting the open/close unit in a closed state.

9. The sperm collection device according to claim 1, wherein inner side surfaces of the core pieces that form the insertion space when the core pieces are closed are composed of soft resin material.

10. The sperm collection device according to claim 2, wherein inner side surfaces of the core pieces that form the insertion space when the core pieces are closed are composed of soft resin material.

11. The sperm collection device according to claim 1, wherein an outer surface of internal portions of the core pieces are composed of hard elastic material and are covered with soft resin material.

12. The sperm collection device according to claim 2, wherein an outer surface of internal portions of the core pieces are composed of hard elastic material and are covered with soft resin material.

13. The sperm collection device according to claim 3, wherein an outer surface of internal portions of the core pieces are composed of hard elastic material and are covered with soft resin material.

14. The sperm collection device according to claim 1, wherein openings are formed on outer peripheral surfaces of the open/close members, and at least a portion of the core pieces is exposed in the openings.

15. The sperm collection device according to claim 2, wherein openings are formed on outer peripheral surfaces of the open/close members, and at least a portion of the core pieces is exposed in the openings.

16. The sperm collection device according to claim 3, wherein openings are formed on outer peripheral surfaces of the open/close members, and at least a portion of the core pieces is exposed in the openings.

17. The sperm collection device according to claim 4, wherein openings are formed on outer peripheral surfaces of the open/close members, and at least a portion of the core pieces is exposed in the openings.

18. The sperm collection device according to claim 5, wherein openings are formed on outer peripheral surfaces of the open/close members, and at least a portion of the core pieces is exposed in the openings.

19. The sperm collection device according to claim 8, wherein the open/close members form a cylindrical hollow portion internally therein when the open/close members are closed.

20. The sperm collection device according to claim 1, wherein portions of the open/close members contact to each other when the open/close members are closed; and
  wherein the contacting portions of the open/close members extend in a longitudinal direction of the cylindrical hollow portion.

* * * * *